(12) United States Patent
Oki et al.

(10) Patent No.: US 8,354,073 B2
(45) Date of Patent: Jan. 15, 2013

(54) INSPECTION CHIP EQUIPPED WITH A LIGHT AMPLIFIER ELEMENT

(75) Inventors: Yuji Oki, Fukuoka (JP); Satoru Kuhara, Fukuoka (JP)

(73) Assignee: Kyushu University, National University Corporation, Fukuoka (JP)

( * ) Notice: Subject to any disclaimer, the term of this patent is extended or adjusted under 35 U.S.C. 154(b) by 1442 days.

(21) Appl. No.: 11/628,306

(22) PCT Filed: May 23, 2005

(86) PCT No.: PCT/JP2005/009364
§ 371 (c)(1),
(2), (4) Date: Dec. 1, 2006

(87) PCT Pub. No.: WO2005/119210
PCT Pub. Date: Dec. 15, 2005

(65) Prior Publication Data
US 2007/0253460 A1      Nov. 1, 2007

(30) Foreign Application Priority Data

Jun. 4, 2004   (JP) ................................. 2004-167297

(51) Int. Cl.
*G01N 15/06*   (2006.01)
*G01N 33/00*   (2006.01)
*G01N 33/48*   (2006.01)

(52) U.S. Cl. ............ 422/400; 422/50; 422/55; 422/68.1; 422/82.05; 422/82.07; 422/82.08; 422/82.09; 422/82.11; 436/43; 436/164; 436/171; 436/172; 73/1.02

(58) Field of Classification Search .................... 422/50, 422/55, 68.1, 82.05, 82.07, 82.08, 82.09, 422/82.11, 400; 436/43, 164, 171, 172; 73/1.02
See application file for complete search history.

(56) References Cited

U.S. PATENT DOCUMENTS 5,690,785 A * 11/1997 Nakaya ............................ 438/8

FOREIGN PATENT DOCUMENTS

| JP | 2001-160642 A | 6/2001 |
|---|---|---|
| JP | 2003-515163 A | 4/2003 |
| JP | 2003-177097 A | 6/2003 |
| JP | 2004-61222 A | 2/2004 |
| JP | 2004-506190 A | 2/2004 |
| JP | 2004-150803 A | 5/2004 |
| JP | 2004-150804 A | 5/2004 |
| WO | WO-01/38857 A1 | 5/2001 |
| WO | WO-02/12862 A1 | 2/2002 |

* cited by examiner

*Primary Examiner* — Brian J Sines
(74) *Attorney, Agent, or Firm* — Birch, Stewart, Kolasch & Birch, LLP

(57) ABSTRACT

The present invention provides an inspection chip using light, which is able to provide an irradiation of light at a high precision. The present invention further provides an inspection chip capable of carrying out the inspection of a sample in a simple manner by using a plurality of lights.

The inspection chip of the present invention comprises a light amplifier element and a sample holding section for holding a sample, in which the light amplifier element is oriented so as to face to the sample holding section, so that the light emitted from the light amplifier element can irradiate the sample held in the sample holding section.

23 Claims, 6 Drawing Sheets

INSPECTION CHIP EQUIPPED WITH A LIGHT AMPLIFIER ELEMENT

FIELD OF THE INVENTION

The present invention relates to an inspection chip and an inspection apparatus, and in particular, to an inspection chip and an inspection apparatus applied for inspecting a substance by detecting light, heat or sound generated from the substance directly or indirectly.

DESCRIPTION OF THE PRIOR ART

An inspection apparatus using the light has been provided to determine the presence or disappearance of a substance and/or to measure a concentration or an alteration of the substance indirectly through the detection of a reaction occurring in the substance when it is subject to the irradiation of a specific light, particularly by detecting absorption of light, fluorescence, phosphorescence, a temperature change, acoustic wave generation, a refraction index change and the like.

An inspection chip used in the inspection apparatus of such type using the light has been more and more miniaturized with the aid of the micro-fabrication in recent years, allowing for an accurate inspection of a sample even in a small amount.

A light source in this application has employed the one using a laser or a light radiation of a laser-like light, which serves as the light source for emitting a light at a specific wavelength for a specific purpose.

However, many of the light sources of the above-described type are bulky, making it difficult to mount them on the inspection chips. The situation has required that the light sources of such type are installed separately from the inspection chips and the light is irradiated onto the chips from the outside. In this case, it is necessary to direct the irradiation of light exactly to a specific region on the inspection chip, but it is not easy to control the direction of the irradiation with high precision in case of the miniaturized chip.

Further, there has been another problem that if the inspection needs a plurality of lights (including the lights having the same or different wavelengths), a plurality of light sources are necessary in association with them, leading to a complicated device. In addition, those light sources are often expensive, and use of the plurality of light sources may result in another problem of higher cost.

On the other hand, a light amplifier element using an optical waveguide has recently drawn more attentions as the element capable of emitting a light having a desired wavelength with the aid of the irradiation of a laser light or the like from the outside (see Patent Document 1).

However, the inspection chip using the light amplifier element as described above is not known.
[Patent Document 1]
 Japanese Patent Laid-open Publication No. 2001-160642

SUMMERY OF THE INVENTION

Problem to be Solved by the Invention

An object of the present invention is to provide an inspection chip using the light, which is able to provide an irradiation of light at a high precision. Another object of the present invention is to provide an inspection chip that allows the inspection of a sample to be carried out easily and conveniently by using a plurality of lights. Still another object of the present invention is to provide an inspection apparatus using the above-described inspection chip.

Means To Solve the Problem

The present invention provides an inspection chip comprising a light amplifier element and a sample holding section for holding a sample, in which the light amplifier element is oriented so as to face to the sample holding section, so that the light emitted from the light amplifier element can irradiate the sample held in the sample holding section.

The present invention further provides an inspection chip as described above, in which the irradiation of the sample with the light induces an energy release from the sample or a chemical or physical structural change in the sample.

Further, the present invention provides an inspection chip comprising a substrate, a light amplifier element formed on the substrate and a sample holding section disposed in the vicinity of the light amplifier element on the substrate for holding a sample, in which the light amplifier element comprises an exciting light waveguide disposed on the substrate and permits a transmission of the exciting light entering from the outside and a laser waveguide disposed on the exciting light waveguide and adapted to emit a specific laser light depending on the exciting light.

Still further, the present invention provides an inspection chip comprising a substrate, a light amplifier element formed on the substrate and a sample holding section disposed in the vicinity of the light amplifier element on the substrate for holding a sample, in which the light amplifier element comprises a laser waveguide disposed on the substrate and adapted to emit a specific laser light depending on the exciting light entering from the outside.

Yet further, the present invention provides an inspection chip as described above, in which the light amplifier element is oriented so as to face to the sample holding section.

Further, the present invention provides an inspection chip as described above, in which the laser light irradiates a sample held in the sample holding section.

Still further, the present invention provides an inspection chip as described above, in which the irradiation of the sample with the laser light induces an energy release from the sample or a chemical or physical structural change in the sample.

Yet further, the present invention provides an inspection chip as described above, in which the energy released from the sample is at least one selected from a group consisting of light, heat and sound.

Further, the present invention provides an inspection chip as described above, in which the energy emitted from the sample is a resultant light from the light of the irradiation that has been transmitted through or reflected by the sample.

Still further, the present invention provides an inspection chip as described above, in which the chemical or physical change in the sample is selected from a group consisting of an electric resistance value, a refraction index, a light transmission factor, a light sensitivity, a carrier mobility, a wavelength dependence of the refraction index, and a wavelength dependence of the light transmission factor so as to inspect the sample.

Yet further, the present invention provides an inspection chip as described above, which comprises a plurality of light amplifier elements.

Further, the present invention provides an inspection chip as described above, in which at least one of the plurality of light amplifier elements emits a light having a wavelength that is different from those from the other light amplifier elements.

Still further, the present invention provides an inspection chip as described above, in which a plurality of light amplifier elements is provided for a single sample holding section.

Yet further, the present invention provides an inspection chip as described above, in which the sample holding section defines an elongated flow channel configuration and each of the plurality of light amplifier elements is disposed along the flow channel.

Further, the present invention provides an inspection chip as described above, in which the substrate has a center of rotation and the sample holding section extends radially from the center of rotation.

Still further, the present invention provides an inspection chip as described above, in which the sample holding section defines flow channels branched in a Y-configuration, and each of the plurality of light amplifier elements is disposed in the respective branched flow channels.

Yet further, the present invention provides an inspection chip as described above, in which the sample holding section defines a circler configuration and each of the plurality of light amplifier elements is disposed around the sample holding section.

Further, the present invention provides an inspection chip as described above, in which a plurality of sample holding sections is formed on the substrate.

Still further, the present invention provides an inspection chip as described above, in which the sample is at least one selected from a biochemical sample group consisting of blood, body fluid, living thing, living body, cell, enzyme, medicine, proteins, peptides, sugars, enzymatic metabolic product, reaction complex, lipids, low-molecular-weight compounds and nucleic acid.

Yet further, the present invention provides an inspection chip as described above, which further comprises an energy detecting section for detecting the released energy.

Further, the present invention provides an inspection apparatus comprising any one of the inspection chips as described above, a laser irradiation section for irradiating the light amplifier element of the inspection chip with a laser, and an energy detecting section for detecting the energy released from the inspection chip.

Still further, the present invention provides an inspection apparatus comprising an inspection chip as described above and a laser irradiation section for irradiating the light amplifier element of the inspection chip with a laser.

Yet further, the present invention provides an inspection apparatus comprising any one of the inspection chips as described above, a laser irradiation section for irradiating the light amplifier element of the inspection chip with a laser, and an energy detecting section for detecting the energy released from the inspection chip, wherein the laser emitted from a single laser irradiation section irradiates a plurality of light amplifier elements.

Effect of the Invention

According to the present invention, it becomes possible to provide an inspection chip using a light, which is capable of irradiating the light with high precision. In addition, according to the present invention, it becomes possible to provide an inspection chip that allows the inspection of a sample to be carried out easily and conveniently by using a plurality of lights.

DESCRIPTION OF REFERENCE NUMERALS

Figure 1:
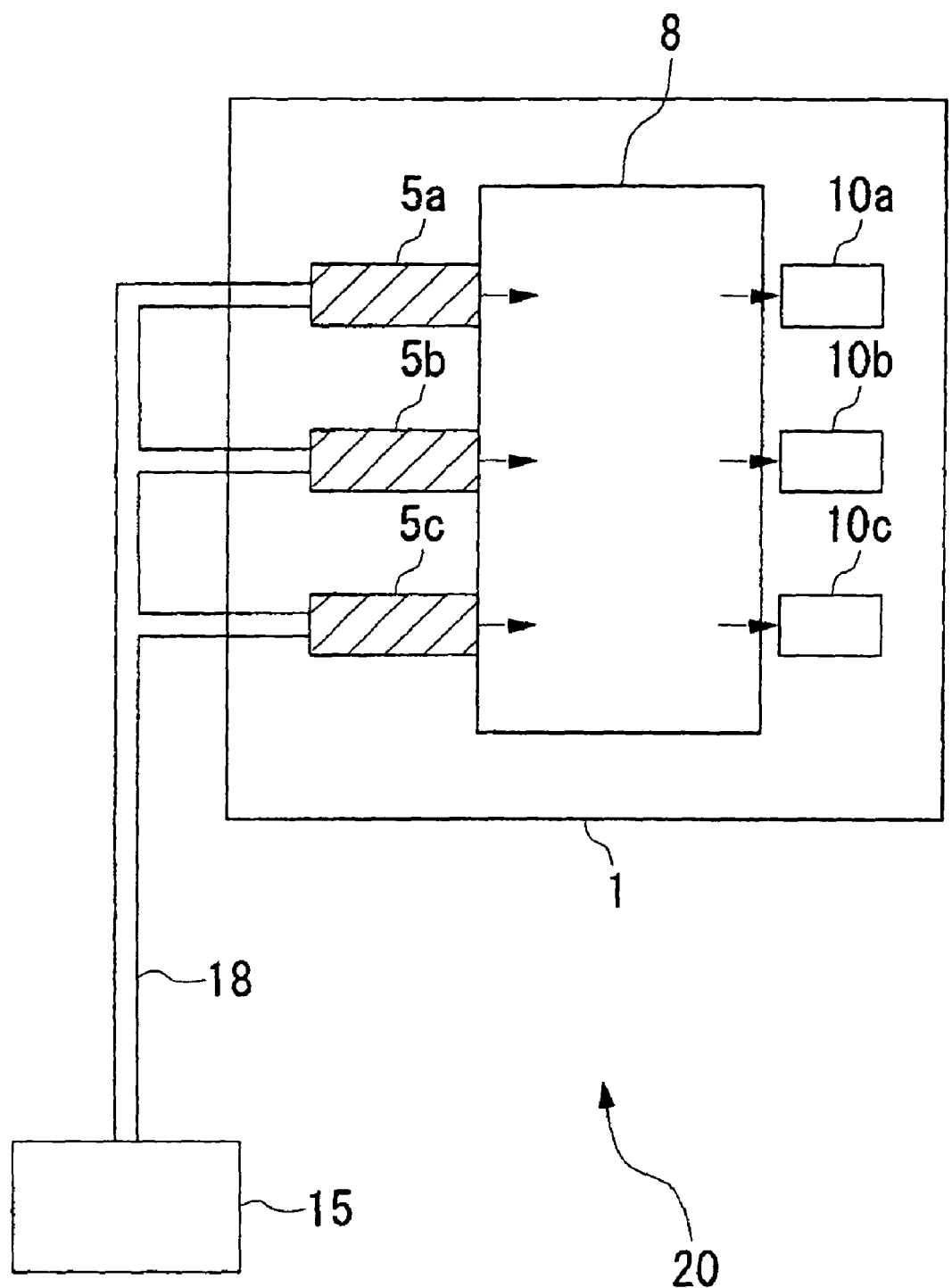
FIG. 1 depicts an example of an inspection chip and an inspection apparatus according to the present invention.

1 Inspection chip
5, 5a, 5b, 5c, 5d, 5e, 5f Light amplifier element
8 Sample holding section
10, 10a, 10b, 10c Energy detecting section
15 Laser light source
18 Optical fiber
20 Inspection apparatus
25 Laser
30 Scanning miller
35 Emitted energy
40 Sample reservoir
45 Sample receiving section
50 Neighboring field light
55 Output light
60 Energy

DESCRIPTION OF THE PREFERRED EMBODIMENTS

For the purpose of the present invention, the term "light amplifier element" refers to an element having a property of emitted a light in response to energy supply and converging the emitted light in a certain direction for radiation of the light.

The light amplifier element used in the present invention may include, for example, an optical waveguide manufactured by using an optically transparent plastic, such as acrylic resin. Specifically, a photo-setting acrylic resin is deposited on a substrate by a thickness in a range of 2 μm to 10 μm, further doped with a pigment, if desired, and then subject to the irradiation of an ultraviolet-ray laser from two directions to cause an interference pattern to be formed therein, and the resultant substrate with the layer is further subject to an appropriate processing, including an etching process, to thereby produce a light amplifier element having a physically or optically diffraction grating. The resultantly obtained light amplifier element is then subject to the irradiation of some kind of energy, such as laser energy, to be modified so that it can allow only the light having a specific wavelength to be fed-back, and thus this filtering effect can help obtain laser oscillations within a narrow spectrum range. By controlling the formation of the interference pattern in this stage, it becomes possible to manufacture the light amplifier element capable of emitting the light having a desired wavelength. According to an alternative manner, a silicon substrate may be used as a mold, on which a waveguide or a branched feature may be fabricated, wherein an optically transparent resin such as acrylic resin doped with a laser pigment can be shaped out of the mold for the fabrication of the light amplifier element. When the light amplifier element is fabricated by using a plastic doped with an organic pigment based on the above-described principle (e.g., a polymer molecule based on poly methyl methacrylate), if the element has partially or entirely a distributed feedback (DFB) structure, the element can turn to be a light amplifier element serving as a waveguide-type solid pigment laser that is capable of oscillating only by being irradiated with an exciting light. The light amplifier element comprises an exciting light waveguide doped with no pigment disposed on a substrate made of plastic and a laser waveguide doped with a pigment disposed on the exciting light waveguide to define the DFB structure. Alternatively, the light amplifier element may comprise a laser waveguide doped with a pigment to define the DFB structure disposed on a substrate made of plastic.

The size of the light amplifier element used in the present invention is not particularly limited so far as it can be accommodated in the inspection chip, and it may be 1 mm to 20 mm long, 1 µm to 1 mm wide and 2 µm to 10 µm thick.

Figure 8:
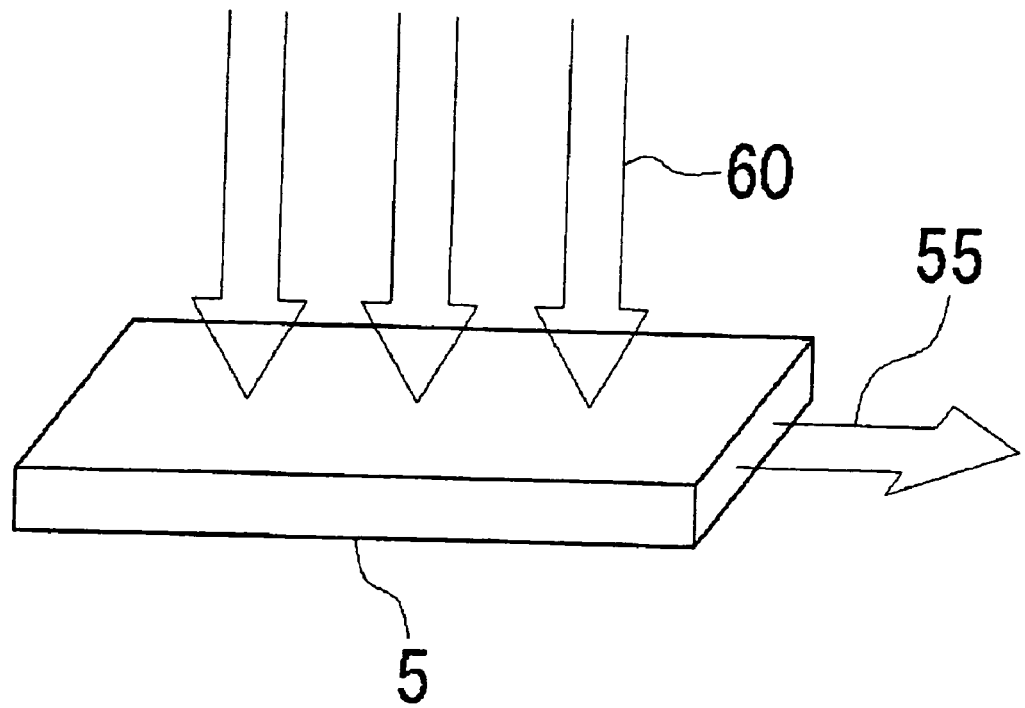
FIG. 8 depicts an operation of a light amplifier element used in the present invention.
Figure 9:
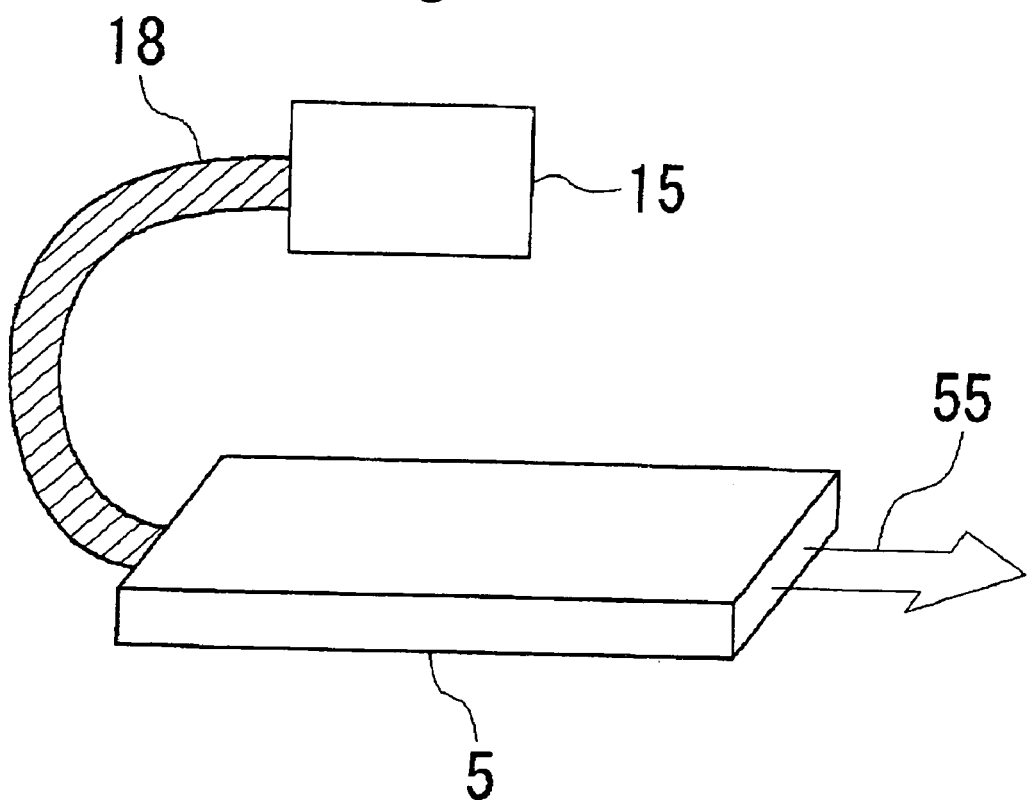
FIG. 9 depicts an operation of a light amplifier element used in the present invention.

FIGS. 8 and 9 depict an operation of the light amplifier element. In FIG. 8, when a light amplifier element 5 is irradiated with energy 60, the energy of irradiation is absorbed into the light amplifier element 5 and results in an output light 55 having a specific wavelength to be released in the direction as shown in the arrow. Further, in FIG. 9, the laser emitted from the laser light source 15 is transmitted through an optical fiber 18 to irradiate the light amplifier element 5, which in turn emits the light of a specific wavelength.

The inspection chip and the inspection apparatus of the present invention will now be described. FIG. 1 is a schematic diagram showing an inspection chip and an inspection apparatus of the present invention. In FIG. 1, an inspection chip 1 of the present invention comprises a light amplifier element 5a, 5b, 5c, a sample holding section 8, and an energy detecting section 10a, 10b, 10c. An end of each light amplifier elements 5a, 5b, 5c is facing to the sample holding section 8. In addition, the light amplifier element 5a, 5b, 5c is connected to the laser light source 15 via the optical fiber 18. It is to be noted that in FIG. 1, the laser light source 15 and the optical fiber 18 construct a laser irradiation section in an inspection apparatus 20 of the present invention.

The inspection chip and the inspection apparatus of the present invention are configured as described above, and an operation thereof will be described below. With reference to FIG. 1, a laser emitted from the laser light source 15 is transmitted through the optical fiber 15 for the irradiation of the respective light amplifier elements 5a, 5b and 5c. Respective light amplifier elements 5a, 5b and 5c that have been irradiated with the laser emit lights, each having a specific wavelength of light to be emitted therefrom, which irradiate a sample held in the sample holding section 8. FIG. 1 is a top view of the chip, in which the sample holding section may define a shallow depression relative to its surrounding area, which may be advantageous for holding a liquid sample therein, for example. The sample irradiated with the light can release the energy corresponding to each specific reaction. The energy released from the sample is detected by each of the energy detecting sections 10a, 10b and 10c for inspecting the sample.

It is to be noted that the energy to be released may include, for example, light such as fluorescence and phosphorescence, heat and sound in addition to the resultant light from the irradiation light that has been transmitted or reflected.

Since a plurality of light amplifier elements are provided for a single sample holding section, it becomes possible to inspect the single sample by concurrently using a plurality of light having different wavelengths. Further, as shown in FIG. 1, if employing such a configuration in which the exciting light from the laser light source 15 may be split in a number of branches for connection corresponding to the number of the used light amplifier elements, then only a single laser emitting device is required as the light source for carrying out the inspection.

Figure 2:
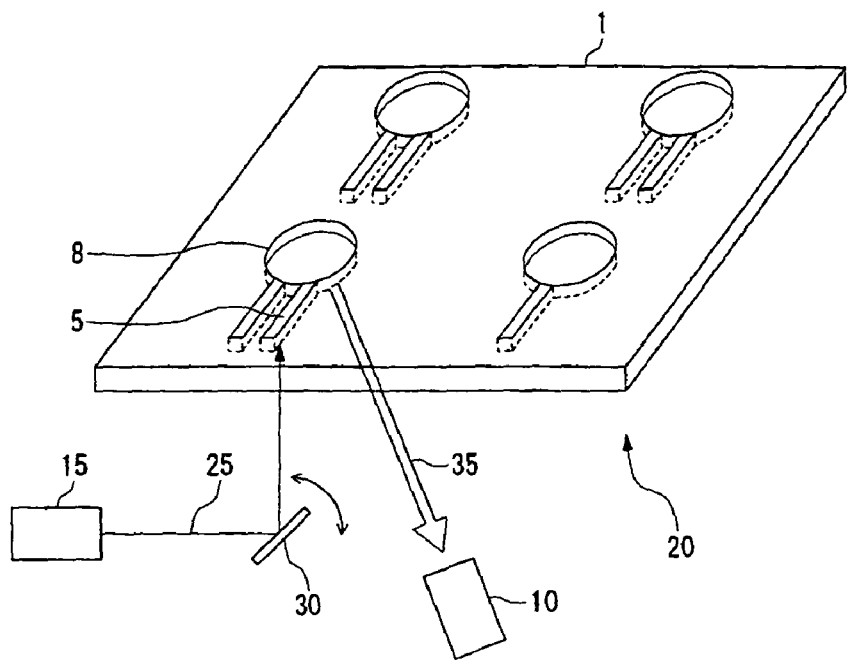
FIG. 2 depicts an example of an inspection chip and an inspection apparatus according to the present invention.

FIG. 2 shows another example of an inspection chip and an inspection apparatus of the present invention. With reference to FIG. 2, the inspection chip 1 of the present invention comprises a plurality of sample holding sections 8, each of the sample holding sections 8 including a single or a plurality of light amplifier element(s) 5 disposed thereon. In the illustrate embodiment, end portions of respective light amplifier elements 5a, 5b and 5c are facing to the sample holding section 8.

With reference to FIG. 2, an inspection apparatus 20 of the present invention comprises a laser light source 15, a scanning miller 30, an inspection chip 1 and an energy detecting section 10.

A laser 25 serving as the exciting light emitted from a laser light source 15 is reflected on the scanning miller 30 and directed to the light amplifier element 5 for irradiation. In FIG. 2, the light amplifier element is irradiated with the laser 25 from its under surface side. The light amplifier element 5 irradiated with the laser 25 emits a light having a specific wavelength, which in turn irradiates the sample held in the sample holding section 8. The ample that has been irradiated with the light releases energy 35, and the released energy 35 is detected by the energy detecting section 10, which is used for carrying out the inspection of the sample.

According to the present invention, the method of scanning with the laser 25 by using the scanning miller 30 allows the irradiation of the laser 5 from the single laser light source 15 to be provided across a plurality of light amplifier elements 5. In addition, including a plurality of sample holding sections along with a plurality of light amplifier elements allows other types of inspections to be carried out with a single inspection chip.

Figure 3:
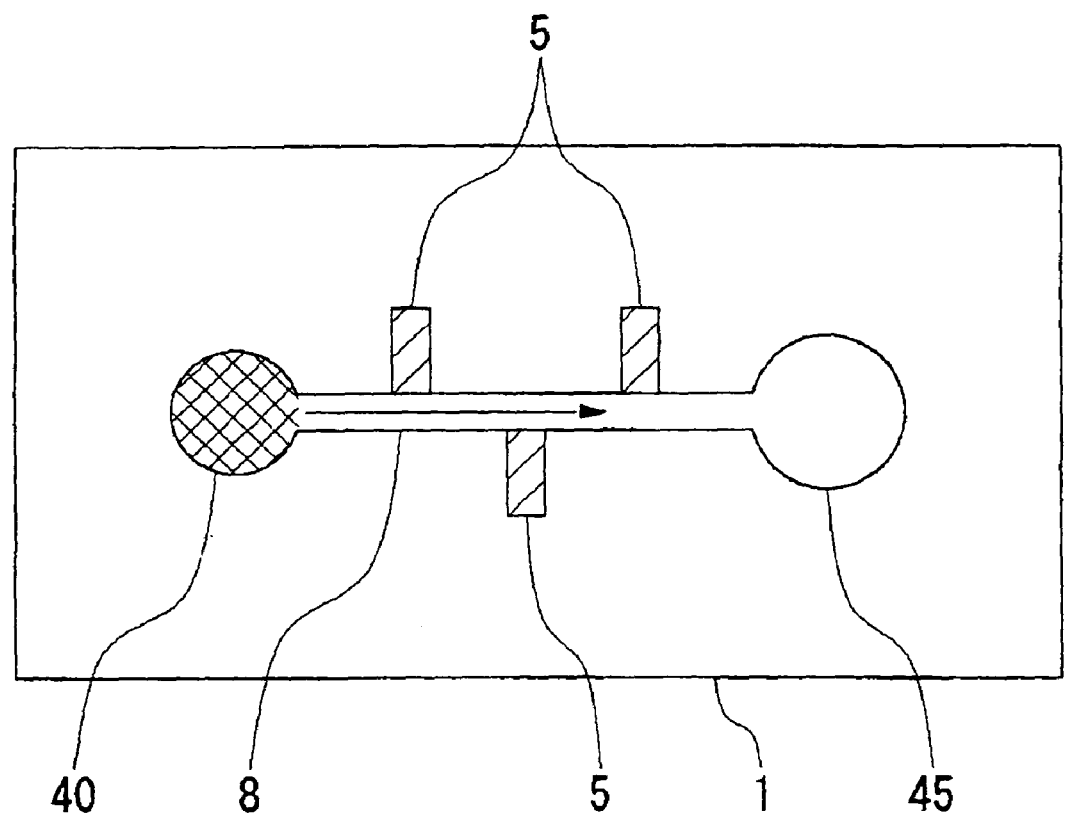
FIG. 3 depicts an example of an inspection chip according to the present invention.

FIG. 3 is a diagram showing another example of an inspection chip. In FIG. 3, the inspection chip 1 of the present invention comprises a sample reservoir 40, a sample receiving section 45, a sample holding section 8 and a light amplifier element 5. A plurality of the light amplifier elements 5 are disposed along a longitudinal direction of the sample holding section 8. End portions of the light amplifier elements 5 are facing to the sample holding section 8.

In FIG. 3, the sample disposed in the sample reservoir 40 is moved through the sample holding section 8 defining an elongated passage to the sample receiving section 45. In this configuration, a laser for excitation irradiates the light amplifier element 5, which in turn emits the light so as to irradiate the sample while the sample is moving through the sample holding section 8. It becomes possible to inspect the sample by detecting the energy released from the sample in response to the laser irradiation.

According to the present invention, since a plurality of light amplifier elements are arranged along the sample holding section 8 from the upstream side (left-hand side in the drawing) toward the downstream side (right-hand side in the drawing), it becomes possible to detect any changes induced in the sample during its flowing or migration.

Figure 4:
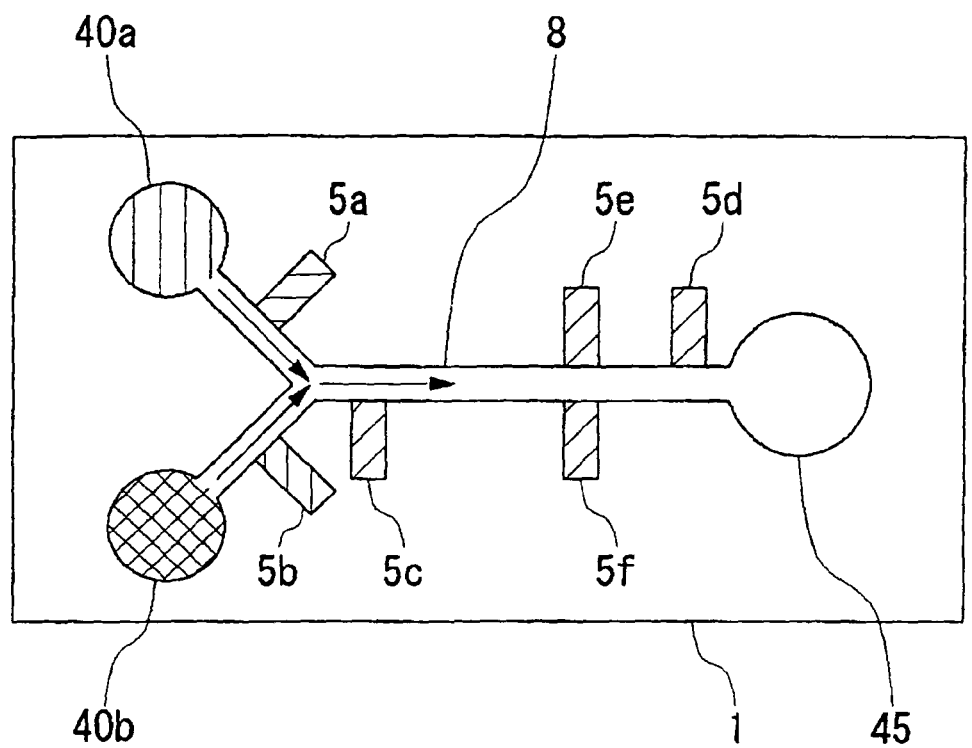
FIG. 4 depicts an example of an inspection chip according to the present invention.

FIG. 4 is a schematic diagram showing another example of the inspection chip according to the present invention. In FIG. 4, the inspection chip 1 of the present invention comprises a sample reservoir 40a, 40b, a sample receiving section 45, a sample holding section 8, a light amplifier element 5a, 5b, 5c,

5*d*, 5*e*, 5*f*. As shown in the drawing, the sample holding section 8 is branched in a Y-configuration. Two sample reservoirs 40*a* and 40*b* are disposed, respectively, in the two branches on the upstream side (on the left-hand side), and the sample receiving section 45 is disposed oppositely on the downstream side (on the right-hand side). In the illustrated example, the light amplifier elements 5*a* and 5*b* are disposed in the two branches of the sample holding section 8, respectively, one in each branch portion. Additionally, four light amplifier elements 5*c*, 5*d*, 5*e* and 5*f* are disposed along the longitudinal direction in the sample holding section 8 extending toward the downstream side. End portions of respective amplifier elements are facing to the sample holding section 8.

In the arrangement of FIG. 4, a first sample placed in the sample reservoir 40*a* and a second sample placed in the sample reservoir 40*b* can be mixed as they are moving through the sample holding section 8. The first and the second samples before being mixed can be inspected by using the light amplifier elements 5*a* and 5*b*, respectively and the sample immediately after being mixed can be inspected by using the light amplifier element 5*c*. Further, a resultant substance from the reaction by the mixing of the first sample with the second sample can be inspected by using the light amplifier element 5*d*.

According to the present invention, any changes in the mixture of a plurality of samples can be detected by using the lights having different, appropriate wavelengths.

Further in the present invention, it becomes possible to control the reaction of the sample by irradiating the sample with the light by using the light amplifier element 5*e*, 5*f*.

Figure 5:
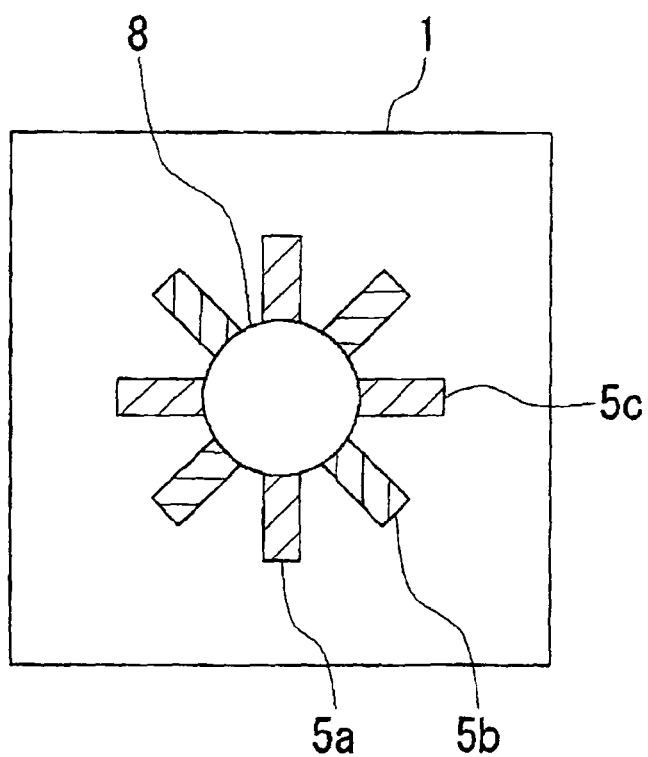
FIG. 5 depicts an example of an inspection chip according to the present invention.

FIG. 5 is a schematic diagram showing another example of an inspection chip of the present invention. In FIG. 5, the inspection chip 1 of the present invention comprises a plurality of light amplifier elements 5*a*, 5*b* and 5*c* and a sample holding section 8. The sample holding section 8 is circular in shape and the light amplifier element 5*a*, 5*b*, 5*c* . . . are disposed radially in the peripheral region of the sample holding section 8, with end portions of the respective light amplifier elements 5*a*, 5*b* and 5*c* facing to the sample holding section. Although eight of the light amplifier elements are shown by way of example only in the drawing, more or less number of light amplifier elements may be used. Although the light amplifier elements 5*a*, 5*b*, 5*c* . . . are respectively arranged in a flat plane, the light amplifier elements may be arranged in a three-dimensional manner. Specifically, one or more light amplifier elements may be disposed below the sample holding section 8 or above 5 the holding section 8 as they cover the holding section 8.

In the present invention, the inspection on a single sample by using a plurality of lights, each having different wavelength, may be feasible by switching the light amplifier elements from 5*a* to 5*b* and then to 5*c* to be used for the irradiation of the laser. Further, switching the light amplifier element currently used for the irradiation of the laser among the elements 5*a*, 5*b* and 5*c* in a short time allows for the inspection adapted for a rapid change. Specifically, the respective light amplifier elements 5*a*, 5*b* and 5*c* may be set so that the oscillation wavelengths from the respective light amplifier elements 5*a*, 5*b* and 5*c* are slightly different from one another. As they are, firstly the light amplifier element 5*a* is irradiated with the laser and subsequently after a period of 1 ns, the light amplifier element 5*b* is irradiated with the light. After another 1 ns (totally 2 ns), the subsequent light amplifier element 5*c* is irradiated with the laser. If the number of scattered particles from the sample under the above-described condition is measured independently based on each of different wavelengths, the inspection of the sample to a degree beyond the time resolution associated with the energy detecting section, such as the photo detector, is feasible. Further, in another example, if the lasers used for the irradiation of respective light amplifier elements 5*a*, 5*b* and 5*c* having different oscillation wavelengths are switched from one another in a short time so as to separate the signals obtained by a single photo detector having no wavelength resolution in terms of time for the signal processing, even the photo detector having no function for the wavelength resolution still can apply the signal to the wavelength resolution for carrying out the inspection of the sample.

Figure 6:
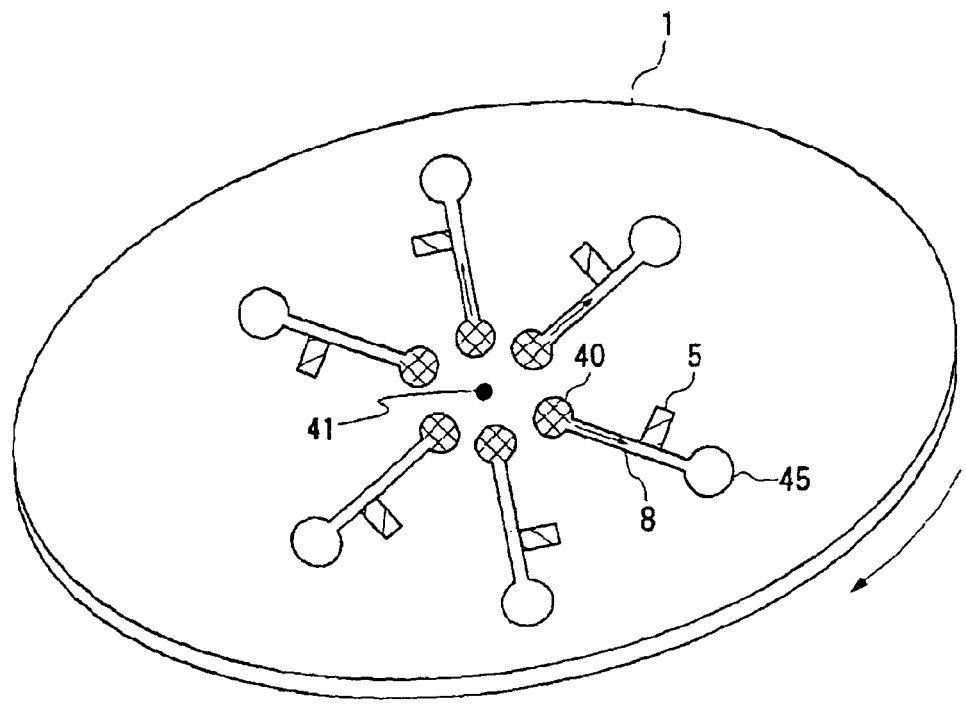
FIG. 6 depicts an example of an inspection chip according to the present invention.

FIG. 6 is a diagram showing another example of the inspection chip according to the present invention. In FIG. 6, the inspection chip 1 of the present invention takes the form of disk and comprises a plurality of sets of components, each set including a sample reservoir 40 in the vicinity of a center of rotation 41, a sample holding section 8 connected at one end to the sample reservoir 40, and a sample receiving section 45 connected to the other end of the sample holding section 8 and located near to the periphery of the disk. Specifically, each sample holding section 8 defines an elongated flow channel extending radially from the center of rotation 41. Further, light amplifier element 5 is disposed in the sample holding section 8 in the vicinity of the sample receiving section 45. End portion of each light amplifier element 5 is facing to the sample holding section 8. Not only one light amplifier element 5 but also a plurality of light amplifier elements 5 may be arranged for each sample holding section 8.

In FIG. 6, when the disk is rotated, the sample disposed in the sample reservoir 40 moves through the sample holding section 8 outwardly in the radial direction into the sample receiving section 45 owing to a centrifugal force generated by the rotation. This makes it possible for the sample to be inspected by using the light amplifier element 5.

The present invention allows the information of the sample, including, for example, a molecular weight of the sample, to be obtained easily. Further, in respective sample holding sections 8, respective different factors in the samples can be inspected separately from one another.

Figure 7:
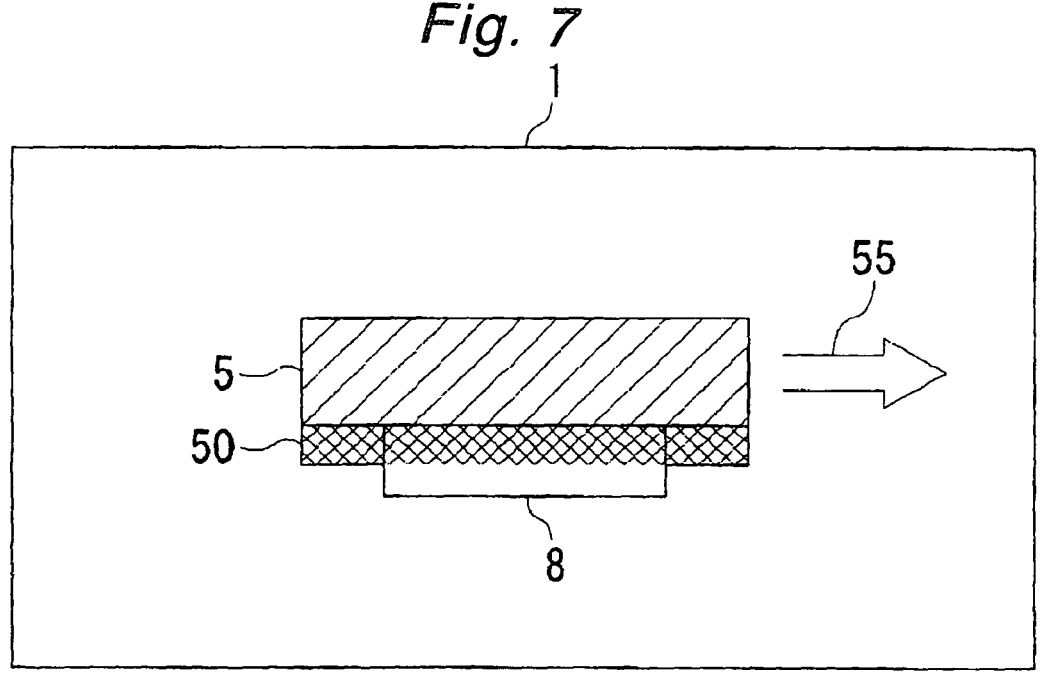
FIG. 7 depicts an example of an inspection chip according to the present invention.

FIG. 7 is a diagram showing another example of the inspection chip according to the present invention. In FIG. 7, the inspection chip 1 of the present invention comprises a light amplifier element 5 and a sample holding section 8 in the vicinity of the side of the light amplifier element 5. In this configuration, end portion of the light amplifier element 5 is facing to the sample holding section 8.

In FIG. 7, when the light amplifier element 5 is irradiated with the laser, an output light 55 is guided in the direction as designated by the arrow for emission of the light. This causes neighboring field light 50 to flow out through the side surface of the light amplifier element 5. The neighboring field light 50 is known to flow out to a region having a distance equivalent to about $1/10$ to $1/2$ of the wavelength of the light emitted from the light amplifier element 5. A sample holding section 8 is held so as to face to a surface of a laser, in which the inspection of the sample can be carried out by irradiating the sample in the holding section 8 located in the vicinity of the laser surface with the neighboring field light 50.

According to the present invention, the inspection across a micro region can be carried out by using the neighboring field light. Further, such an inspection using a change in a refraction index or an absorption coefficient can be also carried out by using a change in the neighboring field light. This is an application for achieving the direct measuring of the refraction index change as in the case with the SPR sensor, which will be described later.

The sample used in the present invention is not limited so far as it can be inspected by using light, including, for example, a biochemical sample, such as a biochemical sample group consisting of DNA, proteins, peptides, sugars, enzymatic metabolic products, reaction complex, lipids, low-molecular-weight compounds and nucleic acid. The inspection can be carried out over a micro sample, such as DNA, with high accuracy by using the present invention.

Figure 10:
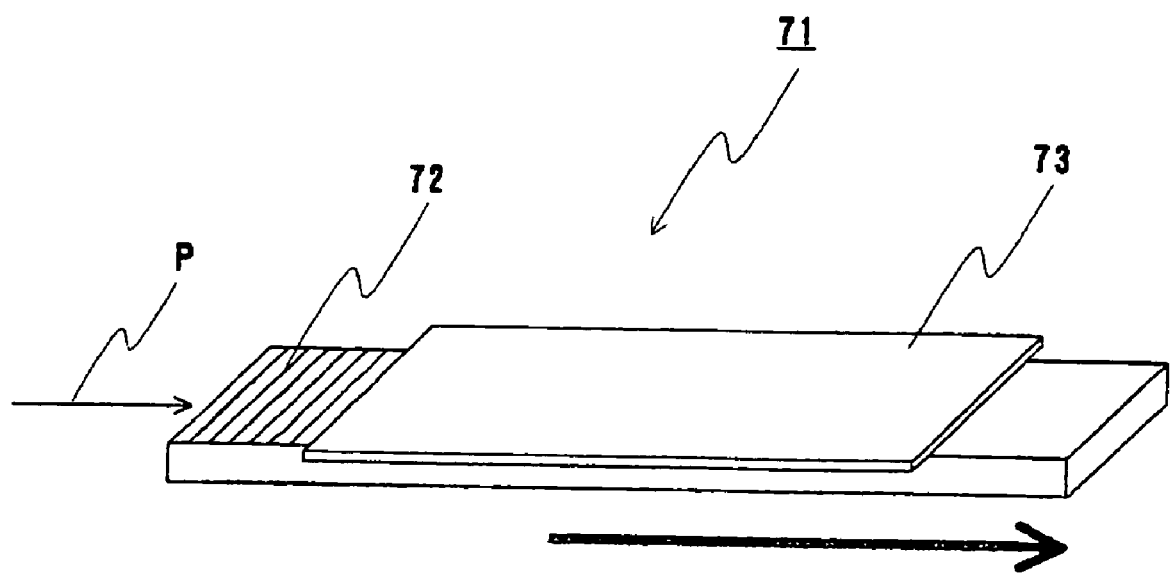
FIG. 10 is a perspective view depicting an exemplary application of the present invention to a SPR sensor.

Although the description has been made in regard to the inspection chip, a surface plasmon resonance (SPR) sensor 71 may be fabricated by using a light amplifier element having a laser waveguide. Specifically, as shown in FIG. 10, a thin film of metal 73 may be formed on top of a laser waveguide 72. Then, an exciting light P is introduced into the light amplifier element. This induces a laser light in the laser waveguide 72, and the laser light tends to attenuate while moving in the direction as designated by the arrow, where the plasmon wave is generated in the surface of the thin film of metal 73. In this connection, a structure for supporting the sample is provided on the surface of the thin film of metal 73, and any refraction index change in this region may be observed by the plasmon resonance. Then, using a manner for changing the wavelength little by little, the inspection is carried out by taking advantage of a phenomenon that an output of the laser at the specific wavelength exhibits a significant attenuation when the SPR condition is satisfied. Unlike the conventional SPR measuring system employing externally a complicated bulky optical system, such a SPR sensor 71 can be implemented on a small chip.

The invention claimed is:

1. An inspection chip comprising a light amplifier element and a sample holding section for holding a sample, wherein
    said light amplifier element modifies an optical characteristic of received light to output light with a modified optical characteristic, and
    a boundary region of the light amplifier element and the sample holding section consists of
        a portion of said light amplifier element which modifies the optical characteristic of received light to output light with the modified optical characteristic, and
        a portion of said sample holding section,
    said light amplifier element being positioned so as to directly face to said sample holding section, so that the light emitted from said light amplifier element directly irradiates the sample held in said sample holding section.

2. An inspection chip claimed in claim 1, wherein the irradiation of said sample with said light induces an energy release from said sample or a chemical or physical structural change in said sample.

3. An inspection chip comprising a substrate, a light amplifier element formed on said substrate and a sample holding section disposed in the vicinity of said light amplifier element on said substrate for holding a sample, wherein
    said light amplifier element modifies an optical characteristic of received light to output light with a modified optical characteristic, and
    a boundary region of the light amplifier element and the sample holding section consists
        a portion of said light amplifier element which modifies the optical characteristic of received light to output light with the modified optical characteristic, and
        a portion of said sample holding section,
    said light amplifier element comprises an exciting light waveguide disposed on said substrate so as to directly face to said sample holding section and permits a transmission of the exciting light entering from the outside and a laser waveguide disposed on said exciting light waveguide and adapted to emit a specific laser light depending on said exciting light.

4. An inspection chip comprising a substrate, a light amplifier element formed on said substrate and a sample holding section disposed in the vicinity of said light amplifier element on said substrate for holding a sample, wherein
    said light amplifier element modifies an optical characteristic of received light to output light with a modified optical characteristic, and
    a boundary region of the light amplifier element and the sample holding section consists of
        a portion of said light amplifier element which modifies the optical characteristic of received light to output light with the modified optical characteristic, and
        a portion of said sample holding section,
    said light amplifier element comprises a laser waveguide disposed on said substrate so as to directly face to said sample holding section and adapted to emit a specific laser light depending on said exciting light entering from the outside.

5. An inspection chip claimed in claim 3 or 4, characterized in that said light amplifier element is oriented so as to face to said sample holding section.

6. An inspection chip claimed in claim 3, characterized in that said laser light irradiates a sample held in said sample holding, section.

7. An inspection chip claimed in claim 6, characterized in that the irradiation of said sample with said laser light induces an energy release from said sample or a chemical or physical structural change in said sample.

8. An inspection chip claimed in claim 2 or 7, wherein said energy released from said sample is at least one selected from a group consisting of light, heat and sound.

9. An inspection chip claimed in claim 2 or 7, wherein said energy emitted from said sample is a resultant light from said light of the irradiation that has been transmitted through or reflected by said sample.

10. An inspection chip claimed in claim 2 or 7, wherein said chemical or physical change in said sample is selected from a group consisting of an electric resistance value, a refraction index, a light transmission factor, a light sensitivity, a carrier mobility, a wavelength dependence of the refraction index, and a wavelength dependence of the light transmission factor so as to inspect said sample.

11. An inspection chip claimed in claim 1, said inspection chip comprising a plurality of light amplifier elements.

12. An inspection chip claimed in claim 11, wherein at least one of said plurality of light amplifier elements emits a light having a wavelength that is different from those from the other light amplifier elements of said plurality of light amplifier elements.

13. An inspection chip claimed in claim 10, wherein a plurality of light amplifier elements is provided for a single sample holding section.

14. An inspection chip claimed in claim 11, wherein said sample holding section defines an elongated flow channel configuration and each of said plurality of light amplifier element is disposed along said flow channel.

15. An inspection chip claimed in claim 14, wherein a substrate has a center of rotation and said sample holding section extends radially from said center of rotation.

16. An inspection chip claimed in claim 11, wherein said sample holding section defines flow channels branched in a Y-configuration, and each of said plurality of light amplifier elements is disposed in the respective branched flow channels.

17. An inspection chip claimed in claim 11, wherein said sample holding section defines a circler configuration and each of said plurality of light amplifier elements is disposed around said sample holding section.

18. An inspection chip claimed in claim 1, wherein a plurality of sample holding sections is formed on a substrate.

19. An inspection chip claimed in claim 1, wherein said sample is at least one selected from a biochemical sample group consisting of blood, body fluid, living thing, living body, cell, enzyme, medicine, proteins, peptides, sugars, enzymatic metabolic product, reaction complex, lipids, low-molecular-weight compounds and nucleic acid.

20. An inspection chip claimed in claim 1, further comprising an energy detecting section for detecting said released energy.

21. An inspection apparatus characterized in comprising an inspection chip claimed in claim 1, a laser irradiation section for irradiating a light amplifier element of said inspection chip with a laser, and an energy detecting section for detecting an energy released from said inspection chip.

22. An inspection apparatus characterized in comprising an inspection chip claimed in claim 20 and a laser irradiation section for irradiating a light amplifier element of said inspection chip with a laser.

23. An inspection apparatus comprising an inspection chip claimed in claim 11, a laser irradiation section for irradiating a light amplifier element of said inspection chip with a laser, and an energy detecting section for detecting an energy released from said inspection chip, said device characterized in that the laser emitted from a single laser irradiation section irradiates a plurality of light amplifier elements.

* * * * *